US010849947B2

(12) United States Patent
Rintola et al.

(10) Patent No.: US 10,849,947 B2
(45) Date of Patent: *Dec. 1, 2020

(54) FEED SUPPLEMENT AND A FEED COMPOSITION COMPRISING RESIN ACID BASED COMPOSITION

(71) Applicants: Hankkija Oy, Hyvinkaa (FI); Forchem Oy, Rauma (FI)

(72) Inventors: Mikko Rintola, Rauma (FI); Juha Orte, Rauma (FI); Juhani Vuorenmaa, Hyvinkaa (FI)

(73) Assignees: Hankkija Oy, Hyvinkaa (FI); Forchem Oy, Rauma (FI)

( * ) Notice: Subject to any disclaimer, the term of this patent is extended or adjusted under 35 U.S.C. 154(b) by 0 days.

This patent is subject to a terminal disclaimer.

(21) Appl. No.: 15/150,537

(22) Filed: May 10, 2016

(65) Prior Publication Data
US 2016/0317595 A1 Nov. 3, 2016

Related U.S. Application Data

(63) Continuation of application No. PCT/FI2014/050832, filed on Nov. 5, 2014.

(30) Foreign Application Priority Data

Nov. 13, 2013 (FI) ..................... 20136113

(51) Int. Cl.
*A61K 31/00* (2006.01)
*A61K 36/15* (2006.01)
*A61K 31/192* (2006.01)
*A23K 50/10* (2016.01)
*A23K 20/158* (2016.01)
*A23K 20/10* (2016.01)
*A61K 31/19* (2006.01)
*A23K 20/105* (2016.01)
*A61K 36/00* (2006.01)

(52) U.S. Cl.
CPC .............. *A61K 36/15* (2013.01); *A23K 20/10* (2016.05); *A23K 20/105* (2016.05); *A23K 20/158* (2016.05); *A23K 50/10* (2016.05); *A61K 31/19* (2013.01); *A61K 31/192* (2013.01); *A61K 36/00* (2013.01); *Y02P 60/56* (2015.11)

(58) Field of Classification Search
None
See application file for complete search history.

(56) References Cited

U.S. PATENT DOCUMENTS

| | | |
|---|---|---|
| 2,240,365 A | 4/1941 | Dreger et al. |
| 2,308,431 A | 1/1943 | Brandt |
| 2,423,236 A | 7/1947 | Harwood et al. |
| 2,481,356 A | 9/1949 | Segessemann et al. |
| 2,530,810 A | 11/1950 | Christenson et al. |
| 2,611,706 A | 9/1952 | Bernhart et al. |
| 2,736,663 A | 2/1956 | Weber et al. |
| 2,854,420 A | 9/1958 | Clark et al. |
| 2,866,739 A | 12/1958 | Ciesielski et al. |
| 2,894,939 A | 7/1959 | Hampton |
| 2,941,941 A | 6/1960 | Groll |
| 2,987,183 A | 6/1961 | Bishop |
| 3,001,962 A | 9/1961 | Carlston |
| 3,009,820 A | 11/1961 | Gould |
| 3,066,160 A | 11/1962 | Hampton |
| 3,141,897 A | 7/1964 | Creclius et al. |
| 3,175,916 A | 3/1965 | Costigliola et al. |
| 3,194,728 A | 7/1965 | Stump |
| 3,257,438 A | 6/1966 | Wicke et al. |
| 3,311,561 A | 3/1967 | Anderson et al. |
| 3,458,625 A | 7/1969 | Ensor et al. |
| 3,691,211 A | 9/1972 | Julian |
| 3,830,789 A | 8/1974 | Garrett et al. |
| 3,887,537 A | 6/1975 | Harada et al. |
| 3,926,936 A | 12/1975 | Lehtinen |
| 4,000,271 A | 12/1976 | Kremer et al. |
| 4,076,700 A | 2/1978 | Harada et al. |
| 4,118,407 A | 10/1978 | Red et al. |
| 4,313,940 A | 2/1982 | Pasarela |
| 4,437,894 A | 3/1984 | Emerson |

(Continued)

FOREIGN PATENT DOCUMENTS

| | | |
|---|---|---|
| CA | 2107647 | 4/1994 |
| CN | 101461433 | 6/2009 |

(Continued)

OTHER PUBLICATIONS

Office Action in co-pending U.S. Appl. No. 15/035,510 dated Feb. 23, 2017.
Finnish Patent and Registration Office Action issued in parent application 20136113 dated Jul. 2, 2014.
International Search Report issued in parent application PCT/FI2014/050832 completed Apr. 8, 2015.
Savluchinski-Feio, S. et al., Antimicrobial activity of resin acid derivatives; Applied Microbiology and Biotechnology, Sep. 2006, vol. 72, No. 3, pp. 430-436.
European Patent Office search report in co-pending European Patent Application 16186985.4 dated Dec. 20, 2016.

(Continued)

Primary Examiner — Jana A Hines
Assistant Examiner — Khatol S Shahnan Shah
(74) Attorney, Agent, or Firm — Merchant & Gould P.C.

(57) ABSTRACT

The present invention relates to a feed supplement which comprises a resin acid based composition comprising over 10% (w/w) resin acids for use in the prevention of growth of harmful bacteria in the animal digestive tract, in the prevention of intestinal disorders, in the modulation of microbial population of the animal digestive tract, in enhancing rumen fermentation, lowering rumen methane production and/or in binding toxins. The invention further relates to a use of the feed supplement and a feed composition comprising the feed supplement.

18 Claims, 1 Drawing Sheet

(56) References Cited

U.S. PATENT DOCUMENTS

| | | |
|---|---|---|
| 4,443,437 A | 4/1984 | Prokosch et al. |
| 4,810,299 A | 3/1989 | Schilling et al. |
| 4,810,534 A | 3/1989 | Seaborne et al. |
| 5,428,072 A | 6/1995 | Cook et al. |
| 5,460,648 A | 10/1995 | Wallach et al. |
| 5,824,322 A | 10/1998 | Balasubramanian |
| 6,020,377 A | 2/2000 | O'Quinn et al. |
| 6,229,031 B1 | 5/2001 | Strohmaler et al. |
| 6,608,222 B2 | 8/2003 | Bonsignore et al. |
| 8,741,171 B2 | 6/2014 | Swift et al. |
| 9,358,218 B2 * | 6/2016 | Vuorenmaa ............ A61K 36/13 |
| 9,422,507 B2 | 8/2016 | Hamunen |
| 2002/0147356 A1 | 10/2002 | Bonsignore |
| 2002/0183298 A1 | 12/2002 | Schersl et al. |
| 2003/0144536 A1 | 7/2003 | Sonnier et al. |
| 2005/0107582 A1 | 5/2005 | Wong et al. |
| 2005/0203279 A1 | 9/2005 | Rojas et al. |
| 2006/0021276 A1 | 2/2006 | Sonnier |
| 2006/0286185 A1 | 12/2006 | Prokosch |
| 2008/0262251 A1 | 10/2008 | Sato et al. |
| 2009/0012164 A1 | 1/2009 | Kelderman |
| 2009/0220638 A1 | 9/2009 | Rerez |
| 2009/0277972 A1 | 11/2009 | Kennon et al. |
| 2009/0285931 A1 | 11/2009 | Shelby et al. |
| 2009/0297687 A1 * | 12/2009 | Ramirez Marco ...... A23L 25/10 426/601 |
| 2011/0045083 A1 | 2/2011 | Bauer et al. |
| 2011/0081442 A1 | 4/2011 | Weill et al. |
| 2011/0200570 A1 | 8/2011 | Mosbaugh et al. |
| 2011/0212217 A1 | 9/2011 | Herranen et al. |
| 2011/0212218 A1 | 9/2011 | Herranen et al. |
| 2012/0070516 A1 | 3/2012 | Tranquil et al. |
| 2013/0041192 A1 | 2/2013 | Saviainen et al. |
| 2013/0131007 A1 * | 5/2013 | Brown ................. A61K 31/714 514/48 |
| 2015/0148416 A1 | 5/2015 | Vuorenmaa et al. |
| 2015/0164966 A1 | 6/2015 | Vuorenmaa et al. |
| 2015/0238454 A1 | 8/2015 | Vuorenmaa et al. |
| 2016/0081368 A1 | 3/2016 | Vuorenmaa et al. |
| 2016/0081952 A1 | 3/2016 | Vuorenmaa et al. |
| 2016/0089407 A1 | 3/2016 | Vuorenmaa et al. |
| 2016/0249645 A1 | 9/2016 | Rintola et al. |
| 2016/0250171 A1 | 9/2016 | Vuorenmaa |
| 2016/0250269 A1 | 9/2016 | Rintola et al. |
| 2016/0287650 A1 | 10/2016 | Rintola et al. |
| 2017/0079944 A1 | 3/2017 | Vuorenmaa et al. |

FOREIGN PATENT DOCUMENTS

| | | |
|---|---|---|
| DE | 10106078 | 9/2002 |
| EP | 0146738 | 7/1958 |
| EP | 0078152 | 5/1983 |
| EP | 1586624 | 10/2005 |
| EP | 2343061 | 7/2011 |
| FI | 20120287 | 4/2013 |
| GB | 955316 | 4/1964 |
| GB | 955316 A * | 4/1964 |
| GB | 2139868 | 11/1984 |
| GB | 2271282 | 4/1994 |
| JP | S60237008 | 11/1985 |
| WO | 9416690 | 8/1994 |
| WO | 9910148 | 3/1999 |
| WO | WO 02/02106 | 1/2002 |
| WO | 03024681 | 3/2003 |
| WO | 2006040537 | 4/2006 |
| WO | 2008099051 | 8/2008 |
| WO | 2008154522 | 12/2008 |
| WO | 2009079680 | 7/2009 |
| WO | 2009106696 | 9/2009 |
| WO | 2011042613 | 4/2011 |
| WO | 2011055018 | 5/2011 |
| WO | 2011080399 | 7/2011 |
| WO | 2011099000 | 8/2011 |
| WO | 2012037297 | 3/2012 |
| WO | 2013060936 | 5/2013 |
| WO | 2013118099 | 8/2013 |
| WO | 2013171370 | 11/2013 |
| WO | 2014184430 | 11/2014 |

OTHER PUBLICATIONS

European Patent Office search report in co-pending European Patent Application 16186994.6 dated Dec. 21, 2016.
European Patent Office search report in co-pending European Patent Application 16187005.0 dated Dec. 21, 2016.
Huwig, et al., Mycotoxin detoxication of animal feed by different adsorbents, Toxicology Letters, Elsevier Biomedical Press, vol. 122, Apr. 30, 2001, pp. 179-188.
Shetty, et al., Saccharomyces cerevisiae and lactic acid bacteria as potential mycotoxin decontaminating agents, Trends in Food Science & Technology, vol. 17, No. 2, Feb. 1, 2006, pp. 48-55.
International Preliminary Report on Patentability in PCT application PCT/FI2014/050832 with a submission date of Sep. 4, 2015.
Office Action in co-pending U.S. Appl. 15/150,561 dated Jun. 20, 2017.
Magee, et al., Composition of American Distilled Tall Oils, JAOCS, vol. 69, No. 4 (Apr. 1992) pp. 321-324.
Antila, M. et al., "The fatty acids of tall oil and their ethyl and glyceryl esters as animal fodder ingredients, the chemical and physical properties of the fatty acid fraction and esters prepared from this fraction", Journal ACTA Agricultureae Scandinavia, 12: 95-105, 1962, Abstract.
Beauchemic, K.A., et al., "Nutritional management for enteric methane abatement: a review", Australian Journal of Experimental Agriculture, 48: 21-27, 2008.
"Carboxylic Acids, Fatty Acids from Tall Oil", Kirk-Othmer Encyclopedia of Chemical Technology, Copyright 1999-2014 by John Wiley and Sons, Inc., 4 pgs.
"Explanatory Notes to the Harmonized Commodity Description and Coding System", The Department of Duty Collection of the 25 General Administration of Customs, China Commerce and TradePress, published on Jan. 31, 2007, see p. 478: "Tall Oil, Whether or Not Refined". English translation of relevant parts.
Grainger, C. et al., "Can enteric methane emissions from ruminants be lowered without lowering their production?", Animal Feed Science and Technology, 166-167: 308-320, 2011.
Machmüller, A. et al., "Potential of various fatty feeds to reduce methane release from rumen fermentation in vitro (Rusitec)", Animal Feed Science Technology, 71: 117-130, 1998.
Bannink et al, A model of enteric fermentation in dairy cows to estimate methane emission for the Dutch National Inventory Report using the IPCC Tier 3 approach, Animal Feed Science and Technology 166-167 (2011), pp. 603-618.
Bergsson, et al. Antibacterial, Antiviral and Antifungal Activities of Lipids, Lipids and Essential Oils as Antimicrobial Agents (2011), pp. 47-80.
De Graaf et al, Consumption of tall oil-derived phytosterols in a chocolate matrix significantly decreases plasma total and low-density lipoprotein-cholesterol levels, British Journal of Nutrition (2002), 88, pp. 479-488.
Duncan, Tall Oil Fatty Acids, Naval Stores (1989), pp. 346-349.
Machmuller, Medium-chain fatty acids and their potential to reduce methanogenesis in domestic ruminants, Agriculture, Ecosystems and Environment 112 (2006) pp. 107-114.
McGuire, et al., Gas Chromatographic Analysis of Tall Oil Fractionation Products After Methylation with N,N-Dimethylformamide Dimethylacetal, Journal of Chromatographic Science, Vo. 36, Feb. 1998, pp. 104-108.
Norlin, Tall Oil, Ullmann's Encyclopedia of Industrial Chemistry, published Online Jun. 15, 2000, pp. 583-596.
Oquinn et al., Effects of modified tall oil versus conjugated linoleic acid on finishing pig growth performance and carcass characteristics, Kansas Agricultural Experiment Station Research Reports, vol. 0, Issue 10 Swine Day (1968-2014), Article 723, pp. 157-161.
O'Quinn et al., Effects of Modified tall oil versus a commercial source of conjugated linoleic acid and increasing levels of modified

(56) References Cited

OTHER PUBLICATIONS tall oil on growth performance and carcass characteristics of growing-finishing pigs, American Socieity of Animal Science, 200, pp. 2359-2368.
O'Quinn et al., Effects of modified tall oil and creatine monohydrate on growth performance, carcass characteristics, and meat quality of growing-finishing pigs, American Society of Animal Science, 2000, pp. 2376-2382.
Patra, Effects of Essential Oils on Rumen Fermentation, Microbial Ecology and Ruminant Production, Asian Journal of Animal and Veterinary Advances 6 (5), 2011, pp. 416-428.
Polan et al., Biohydrogenation of Unsaturated Fatty Acids; Journal of Bacteriology, vol. 88, No. 4, Oct. 1946, pp. 1056-1064.
Smith, et al., Isopimaric Acid from Pinum nigra shows Activity against Multidrug-resistant and EMRSA Strains of *Staphylococcus aureus*, Phytotherapy Research, Phytother, Res. 19, pp. 538-542 (2005).
Snell, et al., Comparative Value of Fatty Acids and Resin Acids of Tall Oil in Soaps, American Oil Chemists' Society, vol. 27, No. 8, Aug. 1950, pp. 289-295.
Sylfat 2LTC Product Data Sheet, Arizona Chemical, Jul. 2009.
Van Nevel, et al., Effect of Fatty Acid Derivatives on Rumen Methane and Propionate In Vitro, Applied Microbiology vol. 21, No. 2, Feb. 1971, pp. 365-366.
Zhou, et al., The Effect of Saturated Fatty Acids on Methanogenesis and Cell Viability of Methanobrevibacter ruminantium, Hindawi Publishing Corporation, Archaea, vol. 2013, Article ID 106916 (http://dx.doi.org/10.1155/2013/106916).
"Explanatory Notes to the Harmonized Commodity Description and Coding System", General Administration of Customs P.R. China, China Commerce and Trade Press, p. 478 (2007), Partial English translation.
Indian Examination Report for corresponding Indian Patent Application No. 201617018910 dated Feb. 4, 2020, 6 pages.
SOderberg, T. et al., "Antibacterial Activity of Rosin and Resin Acids in Vitro", Scand J Plast Reconstr Hand Surg, 24: 199-205 (1990).
Van Immerseel, F. et al., "*Clostridium perfringens* in poultry: an emerging threat for animal and public health", Avian Pathology, 33(6): 537-549 (2004).
European Communication pursuant to Rule 114(2) EPC for corresponding European Patent Application No. 14862579.1 dated Mar. 2, 2020, 17 pages.
European Communication pursuant to Rule 114(2) EPC for corresponding European Patent Application No. 16186985.4 dated Mar. 2, 2020, 16 pages.
Emerstorfer, F. et al., "The role of plant-based antimicrobials in food and feed production with special regard to silage fermentation", Die Bodenkultur, 60(3): 55-65 (2009).
Yadav, S. et al., "Strategies to modulate the intestinal microbiota and their effects on nutrient utilization, performance, and health of poultry", Journal of Animal Science and Biotechnology, 10(2): 1-11 (2019).

\* cited by examiner

FEED SUPPLEMENT AND A FEED COMPOSITION COMPRISING RESIN ACID BASED COMPOSITION

CROSS REFERENCE TO RELATED APPLICATIONS

The present application is a Continuation of International Application PCT/FI2014/050832, filed Nov. 5, 2014, which international application was published on May 21, 2015, as International Publication WO2015/071534. The International Application claims priority of Finnish Patent Application 20136113, filed Nov. 13, 2013, the contents of which are incorporated herein by reference in their entireties.

FIELD OF THE INVENTION

The invention relates to a feed supplement and a feed composition comprising resin acid based composition and to an use of the feed supplement.

BACKGROUND OF THE INVENTION

Imbalances in microbial populations and growth of harmful bacteria in the digestive tract of animals can cause significant losses in animal growth and production. These imbalances manifest themselves as intestinal disorders such as diarrhea. While microbial infections of animals have been prevented by the use of e.g. antibiotics and other agents that prevent the growth of microorganisms, stricter regulations on their use are expected. Ruminant animals can utilize fiber-rich raw materials which have little or no nutritional value for monogastrics like the human. However, the feed conversion efficiency of ruminants is relatively low and their methane production represents a remarkable share of the world's greenhouse gas emissions. With the increasing demand of food there is a need to improve the feed conversion efficiency of ruminants and to lower their methane production. Generally, there is an increasing demand for ingredients for use in animal feeding that can modulate the microbial population in the animal digestive tract but which are readily available, well tolerated and environmentally friendly.

Fractional distillation of crude tall oil (CTO), obtained as a by-product of the Kraft process of wood pulp manufacture, produces depitched tall oil which typically comprises over 10% resin acids and less than 90% fatty acids. Further refinement of depitched tall oil produces tall oil fatty acid (TOFA), Distilled Tall Oil (DTO) and Tall Oil Rosin (TOR) which are available in a variety of compositions differing in the fatty acids and resin acids content. Because TOFA is an inexpensive source of fatty acids, it has previously been used in animal nutrition as an energy source. For instance, GB 955316 discloses the use of alkali metal salts of tall oil fatty acids to improve weight gain and nitrogen retention in ruminant animals.

Toxins are poisonous substances produced within living cells or organisms. Toxins such as mycotoxins are a chemically variable group of secondary metabolites of fungi, which can be found in grains and other feedstuffs even in the absence of any visible fungal growth. High temperature and air humidity during the storage increase the likelihood of fungal growth, but mycotoxin contamination can also occur already in the field. Visible appearance or smell of grains or silage does not indicate the presence or absence of mycotoxin contamination. Effects of toxins such as mycotoxins to farm animals are very variable, and range from increased mortality to decreased fertility and performance. Mycotoxins may also disturb the immune system of animals and make them more susceptible to diseases.

Due to the chemical variability of mycotoxins, analysis of all feedlots for even the most common mycotoxins would be too expensive. Therefore mycotoxin adsorbents are often used to give extra insurance against mycotoxin contamination in feeds. Mycotoxin adsorbents are substances that are itself not digested or absorbed by the animal. They are assumed to bind toxins during the passage through the alimentary canal. Thus, instead of being absorbed by the animals, the toxins get eventually voided via feces.

Toxin binders can also adsorb other types of toxins, like bacterial toxins or secondary metabolites of plants from the digestive tract. Activated carbon (charcoal) is an efficient toxin binder. It is a recommended general toxin binder in various poisonings. However, charcoal also binds vitamins and minerals, which makes it unsuitable for continuous use in feeds.

PURPOSE OF THE INVENTION

The purpose of the invention is to provide a new type of feed supplement comprising resin acid based composition for use in the prevention of growth of harmful bacteria in the animal digestive tract, in the prevention of intestinal disorders, in the modulation of microbial population of the animal digestive tract, in enhancing rumen fermentation, lowering rumen methane production and/or in binding toxins.

SUMMARY

The feed supplement according to the present invention is characterized in that said feed supplement comprises the resin acid based composition comprising over 10% (w/w) resin acids for use in the prevention of growth of harmful bacteria and/or in the prevention of intestinal disorders and wherein the resin acid based composition is Tall Oil Rosin (TOR), Wood Rosin, GUM Rosin and/or Distilled Tall Oil (DTO).

The use of the feed supplement according to the present invention is characterized by using a feed supplement comprising the resin acid based composition comprising over 10% (w/w) resin acids in the modulation of microbial population of the animal digestive tract by increasing the concentrations of acetic and propionic acids and decreasing the concentration of lactic acid, and for improving feed utilization.

The use of the feed supplement according to the present invention is characterized by using a feed supplement comprising the resin acid based composition comprising over 10% (w/w) resin acids in binding toxins.

The use of the feed supplement according to the present invention is characterized in that the toxin is mycotoxin.

The feed composition according to the present invention is characterized in that it comprises a feed supplement in an amount of 0.00001-1.0% (w/w) of the dry weight of the total amount of feed and is used in the prevention of growth of harmful bacteria and/or in the prevention of intestinal disorders.

The use of the feed supplement according to the present invention is characterized in that the feed composition comprises a feed supplement in an amount of 0.00001-1.0% (w/w) of the dry weight of the total amount of feed and is used in the modulation of microbial population of the animal digestive tract by increasing the concentrations of acetic and propionic acids and decreasing the concentration of lactic acid, in enhancing rumen fermentation, lowering rumen methane production and/or in binding toxins.

Figure 1:
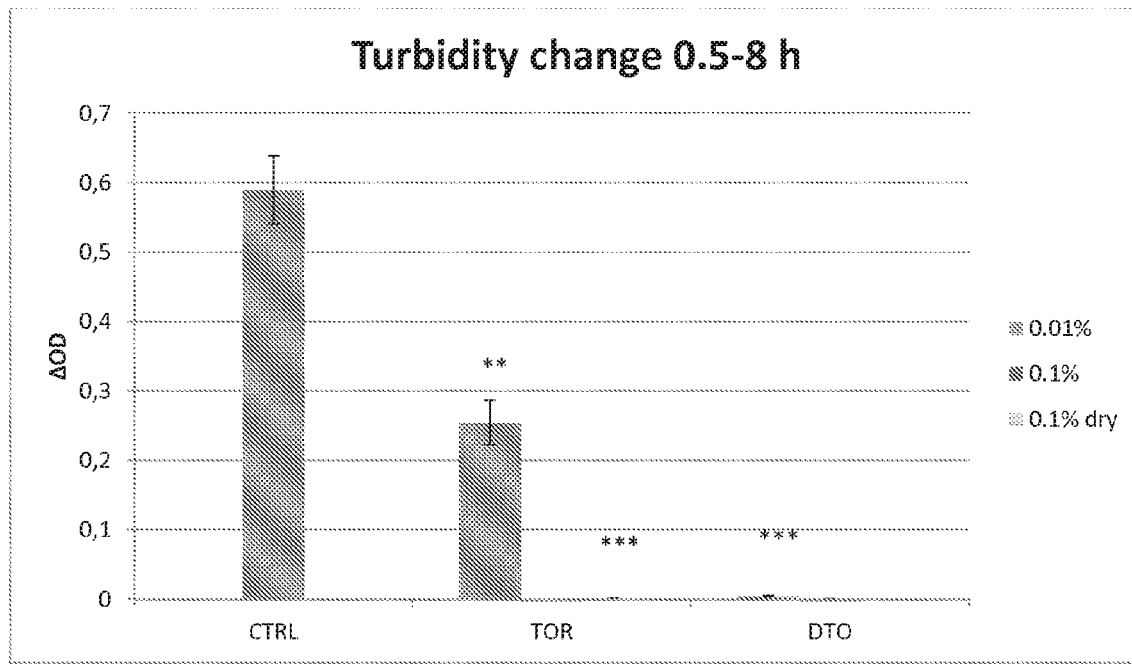
FIG. 1 shows the turbidity change during 8 hours of *Cl. perfringens* growth as a response to a Tall Oil Rosin (TOR) and Distilled Tall Oil (DTO).
Figure 2:
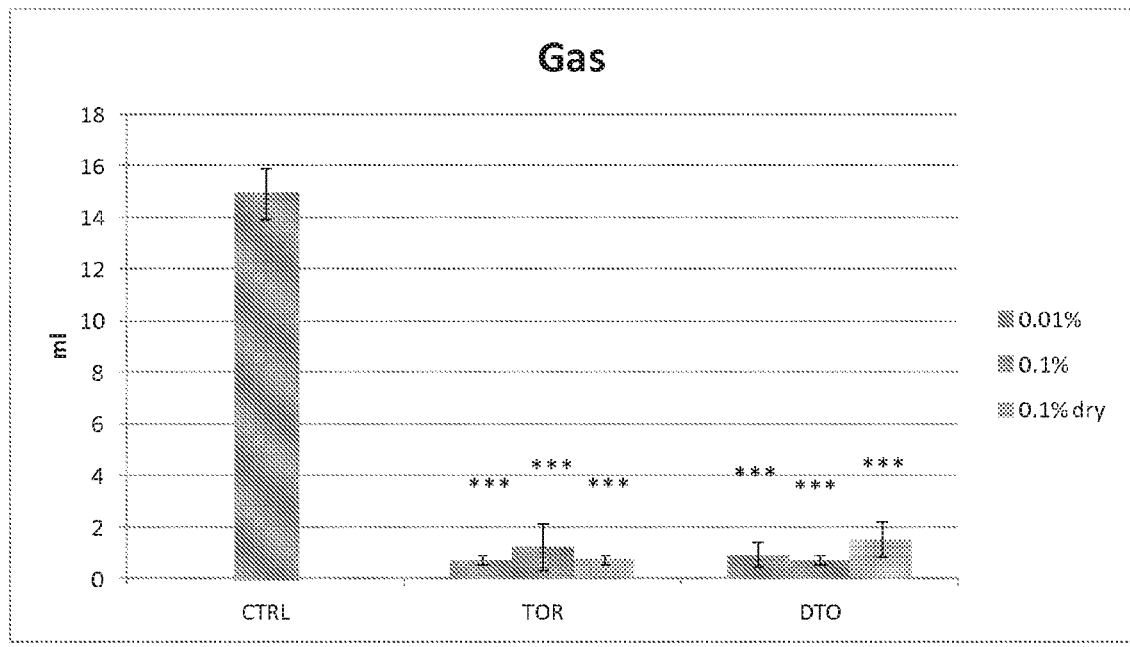
FIG. 2 shows gas production during 8 hours by *Cl. perfringens* growth as a response to Tall Oil Rosin (TOR) and Distilled Tall Oil (DTO).

DETAILED DESCRIPTION OF THE INVENTION

The present invention is based on the realization that a feed supplement which comprises resin acid based composition can be used in the prevention of growth of harmful bacteria in the animal digestive tract, in the modulation of microbial population of the animal digestive tract, in the prevention of intestinal disorders, in enhancing rumen fermentation, lowering rumen methane production and/or in binding toxins.

Resin acids are present in coniferous trees, and there are three main species of resin acid products, namely Tall Oil Rosin (TOR), Wood Rosin and GUM Rosin. TOR is the resin acid fraction separated by vacuum distillation from Crude Tall Oil (CTO) which is produced by the preparation of pulp. CTO is obtained via acidulation of Crude Tall Oil Soap or Crude Sulphate Soap (TOS). TOS is separated from cooking liquid in pulp mill often called black liqueur during pulping process. Wood Rosin is the fraction separated by steam distillation or other means from dead trees, tree stumps, branches etc. and GUM Rosin is the resin fraction that has been steam distilled or separated by other means from resin harvested often called tapping from a living tree.

GUM resin is widely produced in China, Indonesia and Brazil. Wood rosin mainly comes from the USA. TOR is produced in the USA and Scandinavia and to a lesser extent in Central Europe, New Zealand and Russia. Substances containing resin acid and obtained by vacuum distillation from crude tall oil include Distilled Tall Oil (DTO), Tall Oil Fatty Acid (TOFA) and Tall Oil Pitch (TOP). DTO contains 10-40% resin acids. CTO typically contains 15-70% resin acids, and the lowest resin acid contents are generally provided by the cooking of mixed wood pulp.

The term "Tall Oil Rosin" or "TOR" should be understood as referring to a composition obtained by distillation of crude tall oil and further refinement of distilled tall oil. TOR typically comprises 60-99% (w/w) resin acids.

The term "Wood Rosin" should be understood as referring to a composition obtained by distillation or other means from dead trees, tree stumps, branches etc. Wood Rosin typically comprises 50-99% (w/w) resin acids.

The term "GUM Rosin" should be understood as referring to a composition obtained by distillation or separated by other means from resin harvested from a living tree. GUM Rosin typically comprises 50-99% (w/w) resin acids.

The term "Distilled Tall Oil" or "DTO" should be understood as referring to a composition obtained by distillation of crude tall oil and further refinement of distilled tall oil. DTO typically comprises 10-60% (w/w) resin acids.

The resin acid based composition TOR, Wood Rosin, GUM Rosin, CTO, TOS and DTO can also be produced by mixing one or more resin acid compositions and one or more fatty acid compositions in form of oils or fats. Produced resin acid derivatives are for example esters, ethers or alkali metal salts.

Resin acids are known to have antimicrobial, including antibacterial, properties.

The feed supplement of the present invention comprises a resin acid based composition which comprises over 10% (w/w) of resin acids.

In one embodiment of the present invention, the feed supplement comprises a resin acid based composition which comprises over 12% (w/w) resin acids.

In one embodiment of the present invention, the feed supplement is effective in the prevention of growth of harmful bacteria, for prevention of intestinal disorders, in the modulation of microbial population of the animal digestive tract, in enhancing rumen fermentation, lowering rumen methane production and/or in binding toxins.

In one embodiment of the present invention, the feed supplement comprising a resin acid based composition is for use in the prevention of growth of harmful bacteria and/or in the prevention of intestinal disorders.

In one embodiment of the present invention, the feed supplement comprising a resin acid based composition is used in the modulation of microbial population of the animal digestive tract.

In one embodiment the feed supplement is used for improving feed utilization. In one embodiment the feed supplement is used for improving the feed conversion ratio.

In one embodiment of the present invention, the feed supplement comprising a resin acid based composition is used in enhancing rumen fermentation and/or lowering rumen methane production.

In one embodiment of the present invention, the feed supplement comprising a resin acid based composition is used in binding toxins.

In one embodiment, the feed supplement comprising a resin acid based composition is used in binding mycotoxins.

In this context, the term "feed supplement" should be understood as referring to a composition that may be added to a feed or used as such in the feeding of animals.

In this context, the term "resin acids" should be understood as referring to a complex mixture of various acidic compounds derived from wood, specially pine wood. They can also be modified resin acids such as dimers and decarboxylated resin acids. The exact composition of the resin acids present in the resin acid based composition varies e.g. according to the species of the trees the composition is obtained from and the processing conditions under which it is manufactured. Resin acids typically include compounds such as abietic acid, dehydroabietic acid, levopimaric acid, neoabietic acid, pimaric acid and isopimaric acid, only to mention a few.

In the context of the feed additive, the resin acid based composition may be any composition described in this specification.

In one embodiment of the present invention the resin acid based composition of the feed supplement comprises at least one of following resin acids abietic acid, dehydoabietic acid, palustric acid, neoabietic acid, pimaric acid and isopimaric acid and/or derivatives thereof. The derivatives are obtained by modifying the resin acid chemically, biologically or other ways. In one embodiment of the present invention the resin acid based composition comprises at least one of following resin acids abietic acid, dehydoabietic acid, palustric acid, neoabietic acid, pimaric acid and isopimaric acid. In one embodiment of the present invention the resin acid based composition comprises at least one chemically modified resin acid of abietic acid, dehydroabietic acid, palustric acid, neoabietic acid, pimaric acid and isopimaric acid. The resin acid based composition may also be a mixture of unmodified and modified resin acids.

In one embodiment of the present invention the resin acid based composition is Tall Oil Rosin (TOR).

In one embodiment of the present invention the resin acid based composition and/or TOR comprises over 60% (w/w) resin acids. In one embodiment of the present invention the resin acid based composition and/or TOR comprises over 85% (w/w) resin acids.

The TOR can comprise 32-44.5% abietic acid, 18-25% dehydoabietic acid, 0-3% dihydoabietic acid, 3.0-11.5% isopimaric acid, 0-1.5% 8,5-isopimaric acid, 0-2.5% levopimaric acid, 3.3-4% neobietic acid, 7.5-10% palustric acid, 3-4.5% pimaric acid and 0-4.0% sandaropimaric acid. TOR may comprise <0.1% dimers and 0-7% other components.

In one embodiment of the present invention the resin acid based composition is Wood Rosin.

In one embodiment of the present invention the resin acid based composition and/or Wood Rosin comprises over 10 and up to 99% (w/w) resin acids. In one embodiment of the present invention the resin acid based composition and/or Wood Rosin comprises 50-99% (w/w) resin acids.

The Wood Rosin can comprise 45-51% abietic acid, 7.9-8.5% dehydoabietic acid, 0-1% dihydoabietic acid, 11-15.5% isopimaric acid, 0-4.2% 8,5-isopimaric acid, 0-0.2% levopimaric acid, 4.7-7% neobietic acid, 8.2-10% palustric acid, 3-7.1% pimaric acid and 0-2.0% sandaropimaric acid. Wood Rosin may comprise 0-4.2% dimers and 0-1% other components.

In one embodiment of the present invention the resin acid based composition is GUM Rosin.

In one embodiment of the present invention the resin acid based composition and/or GUM Rosin comprises over 10 and up to 99% (w/w) resin acids. In one embodiment of the present invention the resin acid based composition and/or GUM Rosin comprises 50-99% (w/w) resin acids.

The GUM Rosin can comprise 15-45% abietic acid, 3-15% dehydoabietic acid, 0-0.6% dihydoabietic acid, 3.6-28% isopimaric acid, 0-0.3% 8,5-isopimaric acid, 0-1.8% levopimaric acid, 10-19% neobietic acid, 5-25% palustric acid, 2-7.4% pimaric acid and 0-1.5% sandaropimaric acid. GUM Rosin may comprise 0-1.0% dimers and 0-3.5% other components.

In one embodiment of the present invention the resin acid based composition is Distilled Tall Oil (DTO). In one embodiment of the present invention the resin acid based composition is a distillation fraction of Tall Oil. In one embodiment of the present invention the resin acid based composition is a mixture of DTO and a distillation fraction of Tall Oil.

The Distillation fraction of Tall Oil is any resin acids containing fraction of CTO available during CTO refining.

In one embodiment of the present invention the resin acid based composition and/or DTO comprises over 10 and up to 60% (w/w) resin acids. In one embodiment of the present invention the resin acid based composition and/or DTO comprises over 10 and up to 40% (w/w) resin acids.

In one embodiment of the present invention the resin acid based composition is separated from black liqueur during pulping process or TOS or CTO.

The resin acids of the resin acid based composition are insoluble in water. The resin acids of the resin acid based composition may be unmodified or modified.

In one embodiment of the present invention the resin acids of the resin acid based composition and the feed supplement are unmodified. The term "unmodified" should be understood as referring to the resin acid based composition comprising over 10% (w/w) resin acids that is not modified, i.e. treated chemically, or biologically. The feed supplement comprising the resin acid based composition may be used as such.

In one embodiment of the present invention the resin acids of the resin acid based composition are chemically, biologically or other ways modified resin acid compositions. The chemical and/or biological modification of resin acids of the resin acid based composition improves the solubility of its components and resin acids in the digestive tract of an animal. The resin acid based composition may be chemically modified e.g. partially or totally hydrogenated, disportinated, isomerized, oxidized, polymerized, etherified, saponified and/or esterified with suitable compounds, for example, fatty alcohols, glycol, glycerol or glyceridic fatty acid compounds such as mono- di- and tri- and polyglycerides or sugar or polyol based esters. They may be also used as a reactant in Diels-Alder reaction.

In one embodiment of the present invention, the feed supplement comprises a resin acid based composition which is modified by saponification.

Various processes for the saponification of the resin acid based composition using e.g. NaOH or CaOH are known to a person skilled in the art. In one embodiment of the present invention, the resin acid based composition for use according to the present invention is modified by etherification.

In one embodiment of the present invention the resin acid based composition of the feed supplement comprises 1-90 (w/w) fatty acids and/or their derivatives. The fatty acids may be in form of oils or fats or in other forms like free fatty acids or esters, ethers or alkali metal salts or fatty alcohols.

In one embodiment of the present invention, the resin acid based composition includes unsaponifiables which have not an acid group, for example, lipophilic neutral substances and esters from wood. In one embodiment of the present invention, the resin acid based composition includes less than 1% unsaponifiables. The amount of unsaponifiables is typically in DTO products less than 5% and in TOR, Wood and GUM Rosin less than 6%.

In one embodiment of the present invention, the feed supplement comprises resin acid based composition which is dried. The resin acid based composition can be dried by spray drying, drum drying or by any other known suitable drying method.

In one embodiment of the present invention, the feed supplement comprises different active ingredients.

The feed supplement may be added in the feed in a concentration of 0.0001-10 kg//ton of dry weight of the total amount of the feed. The feed supplement comprising the resin acid based composition according to the invention may be added to the feed or feed supplement as such, or it may in general be further processed as desired.

The feed supplement comprising resin acid based composition according to the present invention can be modified into a form which is functional and effective in feeds. Carriers such as oil, fatty acids can be added to the composition for improving the functionality. Further emulgators such as glycerols, lecithin etc. can be added to the resin acid based composition for improving the solubility.

In one embodiments the feed supplement comprising the resin acid based composition according to the present invention may comprise chemically modified resin acid derivatives The resin acid derivatives could also comprise rosin based acid anhydrides, dimers, amines, maleimides, alkenyls, epoxy compositions and/or mixtures thereof or with other suitable chemically modified resin acids known to person skilled in the art.

In one embodiment of the present invention, the feed supplement comprises resin acid based composition which is absorbed into a carrier material suitable for the feed composition such as sugarbeet pulp.

In one embodiment of the present invention, the feed supplement comprises resin acid based composition which is mixed with a liquid carrier material suitable for the feed composition such as vegetable oils or fatty acids.

Further, the feed supplement comprising the resin acid based composition according to the invention may be added to the feed, or it may be administered to an animal separately (i.e. not as a part of any feed composition).

In this context, the term "feed composition" or "feed" should be understood as referring to the total feed composition of an animal diet or to a part thereof, including e.g. supplemental feed, premixes and other feed compositions. The feed may comprise different active ingredients.

The present invention also relates to a feed composition comprising the feed supplement according to the invention.

In one embodiment of the present invention, the feed composition comprises the feed supplement in an amount of 0.00001-1.0% (w/w of the dry weight of the total amount of the feed.

The present invention also relates to a use of the feed supplement according the present invention in a feed composition.

The invention also relates to a method of preventing the growth of harmful bacteria in the animal digestive tract, comprising the step of administering to an animal the feed supplement comprising the resin acid based composition according to the invention.

The invention also relates to a use of the feed supplement comprising the resin acid based composition comprising over 10% (w/w) resin acids in modulating microbial population of the animal digestive tract, preventing intestinal disorders, in enhancing rumen fermentation, lowering rumen methane production and/or binding toxins.

In this context, the term "harmful bacteria" should be understood as referring to any bacteria that is capable of affecting the digestive tract or health of an animal in an adverse manner, including competition for nutrients with the host animal. In this context, the term "microbial population" should be understood as referring to the microorganisms that inhabit the digestive tract, including the Bacteria and Archaea domains and microscopic members of the Eukaryote domain and also intestinal parasites. The microbial population will vary for different animal species depending on e.g. the health of an animal and on environmental factors.

In this context, the term "intestinal disorder" should be understood as referring to various disorders of the digestive tract in an animal, including e.g. diarrhea and other intestinal health problems.

In this context, the term "animal" should be understood as referring to all kinds of different animals, such as monogastric animals, ruminants, fur animals, pets and aquaculture. Non-limiting examples of different animals, including offspring, are cows, beef cattle, pigs, poultry, sheep, goats, horses, foxes, dogs, cats and fish.

In this context, the term "toxin" should be understood as referring to any poisonous substance produced within living cells or organisms. Toxins are products of plants, animals, microorganisms, for example bacteria, viruses, fungi, rickettsiae, protozoa, etc. In this context, the term "mycotoxin" should be understood as referring to a toxic secondary metabolite produced by fungi, such as yeast and mould. The most common mycotoxins in grains or silage are for example aflatoxins, zearalenone, ochratoxin A, deoxynivalenol, fumonisin and T-2 toxin. The toxins will vary depending on environmental factors.

In one embodiment of the present invention, the resin acid based composition is administered to an animal in an effective amount.

The feed supplement comprising the resin acid based composition comprising over 10% (w/w) resin acids is effective in the prevention of growth of harmful bacteria in the animal digestive tract, in the prevention of intestinal disorders, in the modulation of microbial population of the animal digestive tract, in enhancing rumen fermentation, lowering rumen methane production and/or in binding toxins. They have potential in toxin binding.

The present invention has a number of advantages. The feed supplement comprising the resin acid based composition is a readily available, natural, low-cost and environmentally friendly material. Further, it is non-toxic and well tolerated. The feed supplement comprising the resin acid based composition can be used as such. The invention is effective in modulating the composition of the microbiota in the animal digestive tract to a direction that is beneficial for animal performance. Subsequently, other benefits of the invention are e.g. improved animal health and productivity, higher product quality, uniformity, nutritional value and food and product safety, lower costs per production unit and decreased environmental loads. The invention allows the production of feed compositions and supplements at low cost.

The embodiments of the invention described hereinbefore may be used in any combination with each other. Several of the embodiments may be combined together to form a further embodiment of the invention. A product, a method or a use, to which the invention is related, may comprise at least one of the embodiments of the invention described hereinbefore.

EXAMPLES

In the following, the present invention will be described in more detail.

Example 1

Pathogen Inhibition Test

*Clostridium perfringens* is a pathogenic bacterium that causes necrotic enteritis in broiler chicks and other species of poultry. This experiment was conducted to study the inhibition of *Cl. perfringens* by the resin acid based compositions.

Two resin acid based compositions Tall Oil Rosin (TOR) and Distilled Tall Oil (DTO) obtained from Crude Tall Oil distillation were tested as their efficiency against *Clostridium perfringens* growth. The TOR composition contained 88% (w/w) resin acids and the DTO composition contained 27.5% (w/w) resin acids.

| Test compounds | |
|---|---|
| TOR (free resin acids 88%) | 0.03 g of 1:1 in turnip rape oil |
| DTO (free resin acids 27.5%) | 0.015 g |
| TOR (free resin acids 88%) | 0.15 ml of 10% stock solution in ethanol |
| DTO (free resin acids 27.5%) | 0.15 ml of 10% stock solution in ethanol |

-continued

| Test compounds | |
|---|---|
| TOR (free resin acids 88%) | 0.15 ml of 1% stock solution in ethanol |
| DTO (free resin acids 27.5%) | 0.15 ml of 1% stock solution in ethanol |
| ethanol | 0.15 ml ethanol |

The efficiency of test compositions was tested in a *Cl. perfringens* growth inhibition test that measures both the turbidity of the clostridial culture medium as a result of increased number of bacterial cells in a unit volume of medium, and the cumulative gas production during the simulation.

The efficiency of TOR and DTO against the growth of *Cl. perfringens* was tested at concentrations 0.01%. The TOR with 88% resin acid was melted at +105° C. and mixed 1:1 in turnip rape oil, in order to achieve the same runny form as the other two oily products. This diluted product was dosed as double amount in the simulation.

Simulation Procedure:

The simulation was conducted in 25-ml glass bottles containing 15 ml of sterile anaerobic TSGY-media (tryptic soy broth-yeast extract media with glucose) and the bottles were enclosed with air-tight stoppers to ensure anaerobic conditions throughout the experiment. At the beginning of the simulation 0.1% inoculums of the overnight grown *Cl. perfringens* culture was injected to TSGY-bottles. Test compounds, or sterile deionized water for the control treatment, were added in a 150 μl final volume from the respective stock solution according to the treatment. The simulation bottles were randomized to avoid artificial bias between treatments. The bottles were kept at an even 37° C. temperature and mixed 1 min before the turbidity measurement at each time point. The total simulation time was 8 h.

The optical density was measured at the time points of 0.5, 4 and 8 hours. The turbidity (optical density, OD) of growth media increases proportionally as the *Cl. perfringens* cell number and cell density increases.

The total gas production was measured at the end of the 8*h* simulation as an indicator of growth efficiency, since *Cl. perfringens* produces gas due to the active metabolism during exponential growth.

Results

The results are illustrated in FIGS. 1 and 2. The TOR and DTO treatments very effectively inhibited the growth of *Cl. perfringens*, which was detected as the lack of turbidity change (FIG. 1) and the production of negligible amounts of gas (FIG. 2). TOR and DTO compositions inhibited the growth of *Clostridium perfringens* very efficiently regardless of the rosin acid concentration Example 2

Methane Inhibition Test

Two resin acid based compositions Tall Oil Rosin (TOR) and Distilled Tall Oil (DTO) were tested in methane inhibition test. The TOR composition contained 88% (w/w) resin acids and the DTO composition contained 27.5% (w/w) resin acids. The TOR composition containing 88% (w/w) resin acids was mixed 1:1 with turnip rape oil.

The methane inhibition test was conducted with rumen-fistulated dairy cows in order to study the potential of TOR and DTO to decrease the rate of methane production in the rumen. Rumen fluid samples were measured for the numbers of methanogenic bacteria, as they are the methane-producing organisms. The short chain fatty acid profiles, including the concentration of branched chain fatty acids, of the samples were measured as they indicate whether resin based acid compositions had effects to ruminal fermentation.

Three rumen-fistulated, lactating dairy cows were given 3.0 g of dry test compositions/head/day for 21 days, in four portions. TOR and DTO compositions were first dried onto sugar beet pulp and then mixed into the compound feed. Rumen samples were taken before the dietary intervention, once a week during the test composition feeding, and after a two-week washout period. The samples of the trial were analysed for short chain fatty acids (SCFAs) by gas chromatography and numbers of methanogens, protozoa and total bacteria by qPCR.

Results

The results show that the numbers of methane producing bacteria decreased numerically during the TOR and DTO feeding period, while protozoa and the total number of bacteria were not affected by the product. The levels of lactic, propionic, and valeric acids and total short chain fatty acids tended to decrease in the rumen fluid during the TOR and the DTO feeding period. The concentration and relative proportion of branched chain fatty acids tended to decrease as a response to TOR and the DTO.

The experiment shows that the TOR and the DTO lowers the amount of methanogens and thus lowers rumen methane production. The experiment also shows that the TOR and the DTO enhances rumen fermentation.

Example 3

This experiment was conducted to study the effect of saponified DTO with 35% (w/w) resin acids with or without Sugar Beet Pulp (SBP) carrier on the microbial microbial population and fermentation of broiler chick ileum in vitro.

The saponified DTO was manufactured by adding NaOH (sodium hydroxide) to DTO, adding enough water to adjust the total dry matter (DTO) percentage of the mixture to 18-20%, heating the mixture to +90° C., keeping the temperature at +90° C. for 120 minutes, during which time the mixture was gently stirred at 15 min intervals.

Experiment

Ileal contents of 40-days old broiler chicks were used for the simulation media and as inoculants in the simulation models. The trial treatments were prepared from a batch of saponified DTO.

Preparations of DTO with 35% resin acids were produced:

1. Saponified DTO with 20% dry matter content
   An aliquot of the DTO soap was heated to 90° C., mixed with finely ground SBP powder, and dried.
2. Saponified DTO Gastrointestinal Digestion of the Saponified DTO:

Part of the liquid DTO soap and the carrier-absorbed DTO soap was digested by a pepsin-HCl-treatment (pH 2.25) followed by a pancreatin bile-acid-NaOH treatment (pH 6.2) in a dilution series. The digestion was made to evaluate whether the products would resist the conditions of the upper gastrointestinal tract before they enter the distal intestine with higher microbial activity.

The simulation was conducted in a total of 160 2-ml plastic microcentrifuge vials, in 1.5 ml volume, with 10 hours simulation time. Samples were tested at four concentrations of the dry matter of DTO: 0%, 0.005%, 0.01%, 0.01% and 1%.

All the simulation samples were analysed for short chain fatty acids and the total number of microbes. In addition, selected samples were analysed for a number of microbial species or groups by quantitative real-time PCR (qPCR). Ileal simulation samples were analysed for lactobacilli and streptococci.

Results

In the ileal simulation model, DTO soap at 0.5 kg/ton level increased the concentrations of acetic and propionic acids and decreased the concentration of lactic acid. This suggests modulation of microbial metabolism from homofermentative towards heterofermentative metabolical route, which can be seen as a very positive change improving the feed conversion ratio. The sugar beet pulp carrier had little effect on the fermentation Example 4

Test A: Toxin Adsorption into Solid Phase In Vitro

The capacity of a test product to remove toxins from aqueous medium was measured in this test. An efficient toxin adsorbent should be able to bind the toxin in all compartments of the digestive tract, to inhibit the toxin from getting absorbed by the animal. To evaluate the efficacy of the binder in the acidic stomach, the test was run at pH value 2.5 (50 mM glycine-HCl buffer).

The test product was a saponified DTO product which contains 20% resin acids. The saponified DTO was manufactured as in example 3. The product tested was the saponified DTO (20%) with or without silicate carrier.

The test A was conducted with two toxins Ochratoxin A (OTA) and Zearalenone (ZEA), at pH-value 2.5, three test substance levels 0.2, 0.5 and 1 kg/ton and four replicate samples per treatment. Control treatment was replicated 8 times.

Mycotoxins OTA and ZEA were available as 3H-labeled pure compounds, and radioactivity, measured by liquid scintillation counting, was used for their quantification in the samples.

The experiment was conducted in silanized glass vials in 1 ml volume of buffer. In the test system, the bound radioactive toxin becomes removed from the liquid phase through co-pelleting with the insoluble components of the potential binder. The following procedure was used: 1. The test products were weighed into the vials, 2.3H-labeled and intact mycotoxin was mixed with the buffers to get the final toxin concentration of 10 µg/1, 3.1 ml of the buffermycotoxin solution was added to the vials, 4. The vials were sealed and kept for 2 hours at 37° C. in constant slow shaking, 5. The vials were centrifuged for 10 min at 3000×g 6.50 µl of the supernatant was mixed with 150 µl of liquid scintillation cocktail (Optiphase) into wells of a 96-well microtiter plate and 7. The radioactivity of the samples was measured with a liquid scintillation counter for five minutes Results The saponified DTO was able to bind OTA from the aqueous medium statistically significantly, and the binding was dependent on the concentration of the test product. The saponified DTO adsorbed 25-60% of the free OTA from the medium.

The saponified DTO significantly decreased the amount of free ZEA even at the lowest dosages. The saponified DTO removed approximately 30-60% of the free toxin.

It is obvious to a person skilled in the art that, with the advancement of technology, the basic idea of the invention may be implemented in various ways. The invention and its embodiments are thus not limited to the examples described above; instead they may vary within the scope of the claims.

The invention claimed is:

1. A method for modulation of a microbial population of an animal digestive tract, the method comprising administering to the animal an effective amount of a feed supplement comprising tall oil rosin (TOR), wood rosin, GUM rosin, distilled tall oil (DTO), or a mixture thereof, wherein the feed supplement comprises a resin acid based composition, the feed supplement contains over 12% (w/w) resin acids, and the feed supplement is in an amount of 0.00001-1.0% (w/w) of a dry weight of a total amount of feed, and modulating the microbial population.

2. The method according to claim 1, further comprising improving feed utilization.

3. The method according to claim 1, further comprising improving the feed conversion ratio.

4. The method according to claim 1, wherein the resin acid based composition comprises at least one of the resin acids is selected from the group consisting of abietic acid, dehydroabietic acid, palustric acid, neoabietic acid, pimaric acid, isopimaric acid, and derivative thereof.

5. The method according to claim 1, wherein the resin acid based composition is Tall Oil Rosin (TOR).

6. The method according to claim 1, wherein the feed supplement comprises over 60% (w/w) of the resin acids.

7. The method according to claim 1, wherein the resin acid based composition is Wood Rosin.

8. The method according to claim 1, wherein the resin acid based composition is GUM Rosin.

9. The method according to claim 1, wherein the feed supplement comprises over 10 and up to 99% (w/w) resin acids.

10. The method according to claim 1, wherein the resin acid based composition is Distilled Tall Oil (DTO).

11. The method according to claim 1, wherein the feed supplement comprises over 10 and up to 60% (w/w) resin acids.

12. The method according to claim 1, wherein the resin acids are unmodified.

13. The method according to claim 1, wherein the resin acids are modified chemically, biologically or other ways.

14. The method according to claim 13, wherein the resin acids are hydrogenated, disproportined, isomerized, oxidized, polymerized, etherified, saponified and/or esterified and/or used as a reactant in Diels-Alder reaction.

15. The method according to claim 1, wherein the feed supplement comprises 1-90 (w/w) fatty acids and/or their derivatives.

16. The method according to claim 1, wherein the resin acids are modified by saponification.

17. The method according to claim 1, wherein the resin acid based composition is dried.

18. The method according to claim 1, wherein the resin acid based composition is absorbed into a carrier material or mixed with a carrier.

* * * * *